United States Patent
Offermans et al.

(10) Patent No.: US 8,711,356 B2
(45) Date of Patent: Apr. 29, 2014

(54) GAS SENSOR WITH A POROUS LAYER THAT DETECTABLY AFFECTS A SURFACE LATTICE RESONANT CONDITION OF A NANOPARTICLE ARRAY

(75) Inventors: Peter Offermans, Eindhoven (NL); Sywert H. Brongersma, Eindhoven (NL); Mercedes Crego Calama, Geldrop-Mierlo (NL); Gabriele Vecchi, Vespolate (IT); Jaime Gomez Rivas, Eindhoven (NL)

(73) Assignee: Stichting IMEC Nederland, Eindhoven (NL)

(*) Notice: Subject to any disclaimer, the term of this patent is extended or adjusted under 35 U.S.C. 154(b) by 243 days.

(21) Appl. No.: 13/033,180

(22) Filed: Feb. 23, 2011

(65) Prior Publication Data

US 2011/0205543 A1     Aug. 25, 2011

Related U.S. Application Data (60) Provisional application No. 61/307,961, filed on Feb. 25, 2010.

(30) Foreign Application Priority Data

Apr. 13, 2010  (EP) .................................... 10159709

(51) Int. Cl.
    *G01N 21/00*     (2006.01)
(52) U.S. Cl.
    USPC .......................................... 356/437; 356/445
(58) Field of Classification Search
    USPC .......................................... 356/432–444, 445
    See application file for complete search history.

(56) References Cited

U.S. PATENT DOCUMENTS

| | | | |
|---|---|---|---|
| 6,778,316 B2* | 8/2004 | Halas et al. | 359/296 |
| 2006/0034729 A1 | 2/2006 | Poponin | |
| 2007/0148327 A1* | 6/2007 | Baklanov et al. | 427/8 |
| 2007/0188749 A1 | 8/2007 | Brady et al. | |
| 2009/0002701 A1 | 1/2009 | Fattal et al. | |
| 2010/0019155 A1* | 1/2010 | Klunder et al. | 250/363.01 |

FOREIGN PATENT DOCUMENTS

| | | |
|---|---|---|
| WO | 2006/118903 | 11/2006 |
| WO | WO2006/132655 | 12/2006 |
| WO | 2009/016419 | 2/2009 |
| WO | 2009/077557 | 6/2009 |
| WO | WO2010/035232 | 4/2010 |

OTHER PUBLICATIONS

S. Dourdain et al., Determination of porosity of mesoporous silica thin films by quantitative X-ray reflectivity analysis and GISAXS, Sep. 29, 2005, Elsevier, Thin Solid Films 495, 205-209.*

(Continued)

*Primary Examiner* — Tarifur Chowdhury
*Assistant Examiner* — Michael P Lapage
(74) *Attorney, Agent, or Firm* — McDonnell Boehnen Hulbert & Berghoff LLP (57) ABSTRACT

The present disclosure relates to a gas sensor including a first layer and a second layer superimposed on each other along an interface between the two layers. The first layer includes an array of nanoparticles along the interface, the nanoparticles provided so as to allow, upon illumination with electromagnetic radiation, long range diffractive coupling of surface plasmon resonances resulting in a surface lattice resonance condition. The second layer includes a material that, when exposed to at least one predetermined gas, detectably affects the surface lattice resonance condition. The material of the second layer preferably has a porosity of at least 10%.

20 Claims, 7 Drawing Sheets

(56) References Cited

OTHER PUBLICATIONS

G. Fagadar-Cosma, Electrochemical and Spectroscopic Studies of 5,10,15,20-Tetrakis(4-hydroxyphenyl)-21H,23H-porphine, Apr. 19, 2007, Chem. Bull., vol. 52 (66), 1-2, 2007, pp. 109-112.*

Hooper et al., "Sensing using differential surface plasmon ellipsometry," Journal of Applied Physics, vol. 96, No. 5, pp. 3004-3011 (Sep. 1, 2004).

Itagaki et al., "Toxic gas detection using porphyrin dispersed polymer composites," Sensors and Actuators B 108, pp. 393-397 (2005).

Willets et al., "Localized Surface Plasmon Resonance Spectroscopy and Sensing," Annu. Rev. Phys. Chem., 58:267-297 (2007).

Lambeck et al., "Three novel integrated optical sensing structures for the chemical domain," Sensors and Actuators B 113, pp. 718-729 (2006).

Vecchi et al., "Shaping the Fluorescent Emission by Lattice Resonances in Plasmonic Crystals of Nanoantennas," Center for Nanophotonics, FOM Institute AMOLF, c/o Philips Research Laboratories, 6 pages, (Mar. 13, 2009).

Auguie et al., "Collective Resonances in Gold Nanoparticle Arrays," Physical Review Letters (PRL) 101, pp. 143902-1 through 143902-4 (Nov. 3, 2008).

Chen et al., "Three-dimensional composite metallodielectric nanostructure for enhanced surface plasmon resonance sensing," Applied Physics Letters, 94, pp. 073117-1 through 073117-3 (2009).

Numata et al., "Meso-porous membrane of noble metal for surface plasmon resonance gas sensors," Journal of Materials Science, vol. 42, No. 3, pp. 1050-1053 (Jan. 20, 2007).

Kagawa et al., "Compact SPR Gas Sensor for Mobile Robot Olfaction Using Metal Nanostructure and LED Light Source," Sensors, 2007 IEEE, pp. 628-631 (Oct. 28, 2007).

Chu, Yizhuo et al., "Experimental Observation of Narrow Surface Plasmon Resonances in Gold Nanoparticle Arrays", Applied Physics Letters, vol. 93, 181108, (2008), 3 pages.

Jory, M.J. et al., "Surace Plasmon Polariton Studies of 18-Crown-6 Metal-Free Phthalocyanine", J. Phys. D: Appl. Phys., vol. 27, 1994, pp. 169-174.

Jory, M. J. et al., "A Surface-Plasmon-Based Optical Sensor Using Acousto-Optics", Meas. Sci. Technol., vol. 6, 1995, pp. 1193-1200.

Haes, Amanda J. et al., "A Unified View of Propagating and Localized Surface Plasmon Resonance Biosensors", Analytical and Bioanalytical Chemistry, Aug. 27, 2004, pp. 1-22.

* cited by examiner

GAS SENSOR WITH A POROUS LAYER THAT DETECTABLY AFFECTS A SURFACE LATTICE RESONANT CONDITION OF A NANOPARTICLE ARRAY

CROSS-REFERENCE TO RELATED APPLICATIONS

The present application claims priority to U.S. Provisional Patent Application Ser. No. 61/307,961, filed in the United States Patent and Trademark Office on Feb. 25, 2010, and to European Patent Application Serial No. EP10159709.4, filed in the European Patent Office on Apr. 13, 2010, the entire contents of both of which are incorporated herein by reference.

BACKGROUND

1. Field of the Invention

This present application relates to an optical gas sensor. The application moreover relates to a method for optically measuring the presence of a gas using the gas sensor and to a gas sensing system.

2. Description of the Related Art

Figure 1:
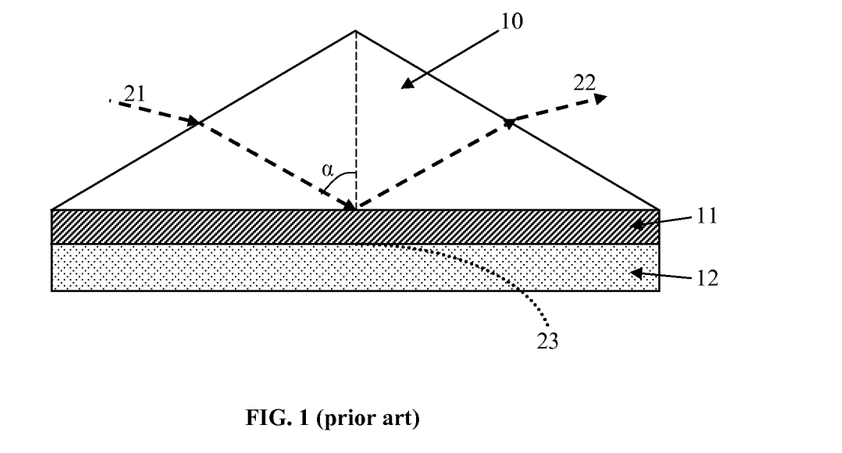
FIG. 1 schematically illustrates the Kretschmann geometry known from the state of the art used in a so-called attenuated total reflection setup.

Surface Plasmon Polaritons (SPP) or Surface Plasmons are electromagnetic waves that can propagate along an interface between two media with dielectric constants of opposite sign, e.g. at the interface between a metal and a dielectric material. They correspond to fluctuations in the electron density at the interface between both materials, for example excited by photons. Typically Surface Plasmon Resonance (SPR) is observed by measuring the reflectivity of p-polarized light of a given wavelength at a metal-dielectric interface for a varying angle of incidence. Alternatively, the angle of incidence is fixed and the wavelength is varied. This is possible by e.g. using the so-called Kretschmann configuration, illustrated in FIG. 1.

In the Kretschmann configuration, a high refractive index prism 10 is placed on a stack of a dielectric layer 12 and a metal film 11 (such as, e.g., a gold film). When light 21 propagating in the prism is incident on the metal film 11 at a large angle of incidence a, it is totally internally reflected, which means that all the light is reflected. There is, however, an evanescent transmitted field 23 that can penetrate the metal film. If the metal film 11 is sufficiently thin, e.g. with a thickness less than 100 nm for visible light, this evanescent field 23 can couple to SPPs on the gold-dielectric interface. When the incident light 21 couples to SPPs the intensity of the reflected light 22 is reduced and results in Attenuated Total Reflection (ATR). The coupling conditions to SPPs depend on the refractive index of the dielectric layer 12. If the refractive index of the dielectric layer 12 changes, the coupling conditions between a light wave and the SPP also change. These include changes are in the angle of excitation of SPPs (α in FIG. 1), the intensity of the reflected light 22, and the wavelength of excitation of SPPs at a specific angle. It is possible to excite SPPs with different wavelengths of light by changing the angle of incidence.

Since the SPPs propagate at the interface between the metal and the dielectric layer, they are very sensitive to changes in this interface. The principle of chemical sensing using SPR involves placing a thin layer of chemically active material (sensing layer, layer 12 in FIG. 1) on the metal surface along which the surface plasmons propagate. The electric and magnetic field of SPPs decay exponentially in the direction perpendicular to the interface. This confinement of the electromagnetic field to the interface is the reason why SPPs can be used as a sensitive tool to detect changes in surface properties. Changes in the sensing layer 12 brought about by the presence of an analyte result in changes in the SPR, which can be monitored, allowing a determination of the analyte concentration. A typical experimentally obtainable resolution of the refractive index of the sensing layer using this method is in the order of $2\times10^{-6}$. Several improvements of the basic SPR technique have been proposed by using improved read-out techniques. Changes in refractive index as small as $10^{-7}$ have been experimentally measured. However, these techniques are not suited for handheld, low power devices as they require a complicated and bulky read-out apparatus.

Several gas sensors based on SPR techniques have also been reported in literature. Typically, the sensing layer is based on redox-active molecules that form charge transfer complexes in the presence of electron-withdrawing and/or electron-donating gases. $NO_2$ is a typical example of such a gas. Phthalocyanines have mainly been used as sensing layers, although porphyrins and their derivatives (or other molecules that form charge transfer complexes) may also be used. Selectivity and sensitivity to certain gases may be achieved by incorporation of side groups or metal ions in the sensing molecules. The formation of charge transfer complexes results in changes of the optical properties of the sensing layer that can be detected with a SPR-based technique.

For example, in "Surface plasmon polariton studies of 18-crown-6 metal-free phthalocyanine", M. J. Jory et al, J. Phys. D: Appl. Phys. 27 (1994) 169-174, SPR in the Kretschmann configuration is used to characterize the response (changes in optical permittivity) of a 14 nm thin film of 18-crown-6 metal-free phthalocyanine upon exposure to 100 ppm $NO_2$ in air. Reflectivity was measured versus the angle of incidence for light of different wavelengths.

In "A surface-plasmon-based optical sensor using acousto-optics", Meas. Sci. Technol. 6 (1995) 1193-1200, a wavelength-tunable optical SPR sensor with a fixed angle of incidence, incorporating an acousto-optic tunable filter (AOTF) is described. The AOTF is used to control the wavelength of a p-polarized light beam incident on a gold-coated diffraction grating. A SPR is observed as a deep minimum in the intensity of the reflected beam as the incident wavelength is varied. By modulation of the AOTF, combined with lock-in techniques, the SPR minimum position can be measured with a precision of 0.0005 nm. The sensitivity of this system was found to be equal to a change in the refractive index of a gas of $1\times10^{-6}$. By adding a chemically active overlayer (18-crown-6 metal-free phthalocyanine) to the system a concentration of 0.01 ppm $NO_2$ in $N_2$ was detected with a response time of about 15 minutes. Although this system provides an improvement as compared to conventional angle-scan systems because the need for a bulky prism and an angle-scan system is avoided, it still requires wavelength modulation by an external AOTF and involves a relatively complicated lock-in technique in order to reach sub-ppm detection levels.

Localized surface plasmon polaritons (LSPP) are surface plasmon polaritons that are localized at the surface of nanoparticles. They exhibit relatively broad resonances compared to SPP, however, they have attracted interest for sensing because they cause large field enhancements in the direct environment of the nanoparticles. This allows them to detect the presence of, for example, (bio)molecules in very small samples as described for example in "A unified view of propagating and localized surface plasmon resonance biosensors", Amanda J. Haes and Richard P. Van Duyne, Anal Bioanal Chem (2004) 379: 920-930. However such sensors based on LSPP show resonances that are much broader than those of SPP-based sensors.

Periodic arrays of metal nanoparticles show sharp resonance peaks in their far field extinction upon irradiation with light. These resonance peaks are called surface lattice resonances and are caused by long range diffractive coupling of localized surface plasmon resonances of the nanoparticles in a periodical array. Long range coupling between the nanoparticles, and therefore surface lattice resonances, are possible when the nanoparticles are sandwiched between dielectric layers with similar refractive index (optically symmetric layers). If there is a large mismatch between the refractive index of the substrate and the surroundings of the nanoparticles, long range coupling is weaker. The spectral position of these resonance peaks is determined by geometrical factors, e.g. the pitch of the nanoparticle array and the shape and size of the individual nanoparticles, and material factors, e.g. the material of which the nanoparticles are formed as well as the refractive index of their surroundings. An example of a gold nanoparticle array and its near field and far field scattering characteristics is reported in "Experimental observation of narrow surface plasmon resonances in gold nanoparticle arrays", Y. Chu et al, Applied Physics Letters 93, 181108 (2008).

DEFINITIONS

Nanoparticle: a particle with dimensions in the range between 5 nm and 500 nm, preferably in the range between 5 nm and 200 nm, having any shape considered suitable by the person skilled in the art, such as for instance round, triangular, or rectangular, and showing localized surface plasmon resonance upon illumination with light.

Surface lattice resonance: spectral resonance arising from diffractive coupling of localized surface plasmon resonances of nanoparticles in nanoparticle arrays. Diffractive coupling occurs at distances between the nanoparticles on the order of the wavelength of the light exciting the localized surface plasmon resonance and is the result of light diffracted in the plane of the nanoparticle array. The coupling, for example, may occur at distances between the nanoparticles of between 100 nm and 1000 nm.

Nanoparticle array: an array, preferably a periodical array, of nanoparticles.

Porosity: the ratio of the volume of the void space in a material with respect to the bulk volume of the material, the bulk volume including the volume of the void space, a smaller porosity denoting a smaller volume of void space.

SUMMARY

It is an aim of the present disclosure to provide a gas sensor, a gas sensing system, and a gas sensing method based on surface lattice resonance for the detection of gases and small molecules with an increased sensitivity, wherein the gas sensor can be compact, has a low complexity, and has a low cost.

The gas sensor according to the present disclosure comprises a first layer and a second layer superimposed on each other along an interface between the two layers. The first layer comprises an array of nanoparticles along the interface. The nanoparticles are provided so as to allow, upon illumination, long range diffractive coupling of surface plasmon resonances resulting in a surface lattice resonance condition, giving rise to sharper resonances than would be obtained for uncoupled nanoparticles. In preferred embodiments of the gas sensor according to the present disclosure, the first layer is sandwiched between the second layer and a third transparent layer, wherein the second layer and the third layer have a substantially matching refractive index. The second layer comprises a material that, when exposed to at least one predetermined gas, detectably affects the surface lattice resonance condition. The second layer has a porosity of at least 10%, enabling penetration of gases and small molecules into the sensing structure and providing a large surface to volume ratio for gas adsorption. It has been found that when molecules of the predetermined gas enter the porous material, the refractive index and/or the extinction coefficient of the porous material changes, leading to a detectable change in the surface lattice resonance condition. Furthermore, the optical properties of the porous material may not only change by the mere presence of gases or small molecules itself, but may also change due to the interactions of these. Since the gas sensor therefore is no longer bound to a contact surface for detecting the gas molecules, as with gas sensors having a non-porous second layer, but instead to a contact volume for detecting the gas molecules, it has been found that the use of a porous second layer increases the sensitivity of the gas sensor with respect to non-porous second layers of the same material.

The evanescent field of the surface lattice resonances may extend up to several hundreds of nanometers perpendicular to the surface of the nanoparticle array, in contrast to that of nanoparticle arrays exhibiting only localized surface plasmon resonance. Therefore, a highest sensitivity may be achieved by increasing the thickness of the second layer to at least the decay length of the evanescent field of the surface lattice resonance. The decay length depends on the size of the nanoparticles, the period of the nanoparticle array, and the refractive index of the second layer and the third layer.

Using a porous second layer also allows increasing the second layer's thickness (and thus the sensitivity) without decreasing the response time of the gas sensor. If a non-porous second layer would be used the sensitivity could be improved by increasing the thickness of the second layer, but increasing the thickness of the second layer would lead to an increase of the response time because an analyte to be sensed needs to diffuse into the second layer and the diffusion time increases with increasing second layer's thickness.

Also, making the second layer porous with a porosity of at least 10%, preferably a porosity of at least 20%, more preferably a porosity of at least 30%, has been found less complex, and less costly than the methods described above to obtain a more sensitive gas sensor. Therefore, the gas sensor according to the current disclosure also has a reduced complexity with respect to known gas sensors having a comparable sensitivity.

In addition it is possible to adapt the porosity and the diameter of the pores in the second layer as a way of discriminating different molecules, including molecules of organic vapors such as alcohols, by their difference in penetration speed.

Furthermore, gas sensitive molecules can be embedded in the porous layer. The inclusion of gas sensitive molecules which change their optical properties by interaction with a gas enables the detection of gases that by their mere presence in the sensing structure do not significantly change the optical properties of the sensing layer.

It is an advantage that a gas sensor according to the present disclosure can be an optically transparent gas sensor which can be read-out by placing it in between a radiation source and a detector and measuring its transmission. The transmission may be measured at the wavelength of the radiation source or the transmission may be measured over a spectral range covering that of the radiation source. Such a configuration has been found more robust than using reflection in, for example, the Kretschmann configuration and therefore more suited for use in, for example, handheld devices.

Moreover, an advantage of using nanoparticles is that surface plasmon resonance is also possible with perpendicularly incident illumination. Since changing the angle of incidence and the wavelength of the incident radiation often requires a sensitive set-up with relatively large power consumption, such a gas sensor is more suited for handheld devices and/or devices needing low power consumption. Illumination under angle is, however, possible and will shift the plasmon resonances to larger wavelengths.

Due to the enhancement of the optical near field in the proximity of nanoparticle arrays, the change in resonance condition of the nanoparticles upon gas exposure and therefore its effect on the extinction spectrum of the nanoparticle array, can be stronger than the change in extinction spectrum of porous dielectric layers with embedded gas molecules without nanoparticle arrays.

The nanoparticle arrays moreover allow to select the lattice resonance condition to occur at any angle of incidence before and after gas exposure at the wavelength of the incident electromagnetic radiation by changing the geometrical factors of the nanoparticle array itself, such as, for example, array pitch in different directions, shape, size of the nanoparticles, etc. Therefore it becomes possible to measure the change in the resonance condition upon gas exposure by measuring the transmission of the nanoparticles at the wavelength of the incident electromagnetic radiation.

In preferred embodiments of the gas sensor according to the present disclosure, the nanoparticles are made of a metal which has a dielectric constant having an opposite sign of the dielectric constant of the material of the second layer, for example, a dielectric material.

In further embodiments of the gas sensor according to the present disclosure, the metal is gold. However, other metals such as silver or aluminum are also possible.

In embodiments of the gas sensor according to the present disclosure, the nanoparticles are made of a material having a complex permittivity with an imaginary part larger than or similar to the real part, e.g. an absorbing material, for example silicon, germanium, a phase change material, a chalcogenide glass, or absorbing polymers (as described in PCT/IB2009/054181).

In preferred embodiments of the gas sensor according to the present disclosure, the material of the second layer is a dielectric material.

In preferred embodiments of the gas sensor according to the present disclosure, the gas sensor comprises a plurality of said nanoparticle arrays, each having different lattice resonance conditions. Such a gas sensor allows the detection of changes in resonance conditions in a more accurate manner than would be possible with a single nanoparticle array. By using multiple arrays of nanoparticles it becomes possible to, for example, measure concentration of the gas to which they are exposed or measure the duration of the gas exposure. For example, given a predetermined source of electromagnetic radiation, at the wavelength of incident electromagnetic radiation the first array might be in a surface lattice resonance condition before gas exposure whereas the last array is not, while the last array might be in a surface lattice resonance condition after gas exposure whereas the first array is no longer in a surface lattice resonance condition. Additional arrays in between the first and the last may be tuned to come sequentially to their surface lattice resonance condition during the gas exposure. This way concentration, gas propagation, etc. can also be determined.

In preferred embodiments of the gas sensor according to the present disclosure, the first layer is sandwiched between the second layer and a third transparent layer offering optical symmetry. Preferably the third layer and the second layer have substantially the same optical properties. The material of the third layer can be the same as the material of the second layer. The third layer can be a porous layer, e.g. having a same porosity as the second layer.

In embodiments of the gas sensor according to the present disclosure, the first layer comprises the material of the second layer between the nanoparticles. Preferably, the material of the second layer completely fills up the space between the nanoparticles. However, it is also possible that the material of the second layer only partially fills up the space between the nanoparticles and that, for example, different layers of different materials are present between the nanoparticles. For example, the space between the nanoparticles can be filled up with a first intermediate layer adjacent to the second layer and made of the material of the second layer and a second intermediate layer superimposed on the first intermediate layer adjacent to the third layer and made of the material of the third layer.

However, the gas sensor in which the space between the nanoparticles is completely filled with the material of the second layer may be preferred as it is easier to manufacture by creating the third layer e.g. on a transparent substrate, after which the nanoparticles are deposited on the third layer and finally depositing a second layer on top of the first layer such that the material of the second layer also fills up the spaces between the nanoparticles.

In preferred embodiments of the gas sensor according to the present disclosure, the third and the second layer are substantially optically symmetric to increase the long range coupling between the nanoparticles.

The third layer and/or the second layer can comprise a stack of layers, i.e., the third layer and/or the second layer can comprise different layers, e.g. made of a different material or e.g. having a different porosity.

In preferred embodiments of the gas sensor according to the present disclosure, the third and the second layer have a thickness that is equal to at least the decay length of the evanescent field of the surface lattice resonance, which may be on the order of several hundred nanometers, enabling sharp resonances.

In preferred embodiments of the gas sensor according to the present disclosure, the second porous layer comprises gas sensitive molecules such as for example redox-active molecules such as for example porphyrin molecules, such as 5,10,15,20-Tetrakis(4-hydroxyphenyl)-21H,23H-porphine. The inclusion of gas sensitive molecules that change their optical properties by interaction with certain gases enables the detection of gases that by their mere presence in the sensing structure do not significantly change the optical properties of the sensing layer. Such a gas sensor can be used for detecting electron accepting and electron reducing gases, i.e., gases that interact with the redox-active molecules and therefore may be detected from a change in optical properties of a sensing layer comprising these redox-active molecules. Examples of gases that may be detected are $NO_2$, $SO_2$, HCl, NO, $CO_2$, CO, $NH_3$. The second porous layer moreover creates an enlarged surface at which the gas sensitive molecules are located, enabling an increase of the adsorption sites for gas molecules. Therefore, the sensitivity and response time of the gas sensor is considerably increased without having to substantially increase the complexity, cost, and/or size of the gas sensor. For example it has been found that it is possible to detect molecules of gases having a refractive index close to the surrounding gas, which often is atmospheric air.

In preferred embodiments of the gas sensor according to the present disclosure, the second layer comprises open pores offering improved diffusion qualities such that the detection of gases is further improved.

In preferred embodiments of the gas sensor according to the present disclosure, the second layer is a nano clustered silica layer such as for example described in WO 2006/132655.

The disclosure also relates to a method for optically measuring the presence of a gas using the gas sensor according to embodiments of the present disclosure, wherein the gas sensor is illuminated with electromagnetic radiation from a radiation source and wherein a detector analyzes at least part of the electromagnetic radiation transmitted through the gas sensor. The detector may measure the transmitted radiation at the wavelength of the radiation source or it may measure the transmitted radiation over a spectral range covering that of the radiation source.

The disclosure also relates to a gas sensing system, comprising a gas sensor according to the disclosure, a source of electromagnetic radiation for illuminating the gas sensor and a detector for analyzing at least part of the electromagnetic radiation resulting from the illumination of the first layer and transmitted through the gas sensor, the detector being provided to detect changes in the transmitted electromagnetic radiation. The changes may be measured at the wavelength of the radiation source, or over a spectral range covering that of the radiation source.

The subject matter regarded as invention is particularly pointed out and distinctively claimed in the claim section concluding this document. The invention however, both as to organization and method of operation, together with features and advantages thereof, may best be understood by reference to the following detailed description when read with the accompanying drawings.

BRIEF DESCRIPTION OF THE SEVERAL VIEWS OF THE DRAWINGS

The disclosure will be further elucidated by means of the following description and the appended figures.

FIGS. 7(a)-7(b) illustrate changes in surface lattice resonance before and after $NO_2$ gas exposure.

DETAILED DESCRIPTION

In the following detailed description, numerous specific details are set forth in order to provide a thorough understanding of the invention and how they may be practiced. However, it will be understood that the present invention may be practiced without these specific details. In other instances, well-known methods, procedures, and techniques have not been described in detail, so as not to obscure the present invention. While the present invention will be described with respect to particular embodiments and with reference to certain drawings, the invention is not limited hereto. The drawings included and described herein are schematic and do not limit the scope of the invention. It is also noted that in the drawings, the size of some elements may be exaggerated and, therefore, not drawn to scale for illustrative purposes.

Furthermore, the terms first, second, third, and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the disclosure described herein are capable of operation in other sequences than described or illustrated herein.

Moreover, the terms top, bottom, over, under, and the like in the description and the claims are used for descriptive purposes and not necessarily for describing relative positions. It is to be understood that the terms so used are interchangeable under appropriate circumstances and that the embodiments of the disclosure described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B.

Figure 2:
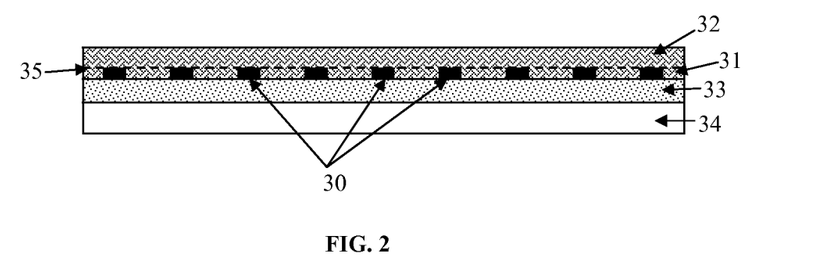
FIG. 2 schematically shows a cross section of a gas sensor according to an embodiment of the present disclosure.

A cross section of a gas sensor according to an embodiment of the present disclosure is schematically shown in FIG. 2. On a transparent substrate 34 (such as, e.g., a glass substrate, a quartz substrate, or a plastic substrate) a third dielectric layer 33 and a second dielectric layer 32 are provided. Between the second dielectric layer 32 and the third dielectric layer 33 a first layer 31 is present. The first layer 31 comprises an array of nanoparticles 30 along an interface 35 between the two layers 31, 32. In between the nanoparticles 30 the same material as the material of the second dielectric layer 32 is preferably present. Alternatively, in between the nanoparticles 30 a dielectric material different from the material of the second dielectric layer 32 can be present.

The nanoparticles 30 may, for example, have a size in the range between 10 nm and 1000 nm and the distance between the nanoparticles 30 may, for example, be in the range between 100 nm and 1000 nm, e.g. in the range between 300 nm and 600 nm. In the final device, the second dielectric layer 32 is used as a sensing layer. The third dielectric layer 33 is, for example, provided for creating an optically symmetric environment for the nanoparticles 30. Therefore, the third dielectric layer 33 and the second dielectric layer 32 preferably have a same index of refraction. The third dielectric layer 33 and the second dielectric layer 32 can be made of the same material or they can be made of a different material. The thickness of the third dielectric layer 33 and of the second dielectric layer 32 is preferably selected such that influences from the substrate 34 and from the environment (above the second dielectric layer or sensing layer 32) are either eliminated or substantially reduced. For example, the thickness of these layers may be on the order of 500 nm.

In embodiments of the present disclosure wherein the transparent substrate 34 and the second dielectric layer 32 have the same index of refraction, the additional third dielectric layer 33 may be omitted and the array of nanoparticles 30 may be provided at the interface between the transparent substrate 34 and the second dielectric layer 32.

The second dielectric layer 32 is preferably a porous layer such as e.g. a nano clustered silica or NCS layer (as e.g. described in WO 2006/132655). The pores of this porous layer are preferably open pores, i.e. the pores are preferably interconnected. The porosity of the second dielectric layer or sensing layer 32 is preferably sufficiently high to allow fast gas diffusion into the sensing layer 32. The porosity of the sensing layer 32 can be larger than 30%. However, lower porosities may also be used such as, for example, porosities of at least 10% or 20% (e.g. in cases where the speed of diffusion of different gases is monitored). NCS, for example, has a porosity of up to 30% and a pore size of 1 nm to 2 nm. However, porosities larger than 30% are also possible such as, for example, porosities of at least 40%, 50%, 60%, 70% or even higher.

A lower porosity leads to a slower penetration of vapors and gasses whereas a higher porosity may imply a larger pore size, which would weaken the differences in penetration speed of different vapors or gases. A larger pore size would also lead to a smaller surface to volume ratio. As most probably the sensing molecules are located at the surface of the pores, this would lead to a reduction of the amount of sensing molecules and adsorption locations of gas molecules, and thus sensitivity. The porosity therefore preferably is selected depending on, for example, the desired sensitivity, gasses to be detected, etc.

Due to the porosity of the second dielectric layer 32, the penetration of gases and vapors (e.g. gases and vapors to be detected by the optical sensor) into this dielectric layer is enabled. The penetration of certain gases and vapors may change the refractive index of the porous dielectric layer 32, which leads to a change in the surface lattice resonance condition of the nanoparticle array. This change may be detected by measuring the far field extinction spectrum of the nanoparticle array. The porosity of the second dielectric layer 32 and the diameter of the pores in the second dielectric layer 32 can be used as a way of discriminating different vapors by their difference in penetration speed. However, the change in refractive index of the porous dielectric material by penetration of gases such as $NO_2$, $CO_2$, CO, $NH_3$, $SO_2$ etc. may be very small, which may limit the detection of these gases to very high concentrations only. Therefore, to increase the sensitivity and at the same time, the selectivity to these gases, gas-sensitive molecules (such as e.g. phthalocyanines, porphyrins etc.) are embedded in the porous dielectric layer 32. These gas-sensitive molecules (e.g. Porphyrin molecules, such as e.g. 5,10,15,20-Tetrakis(4-hydroxyphenyl)-21H, 23H-porphine (2H—OHTPP)) show a change in their optical properties (e.g. absorption spectrum) upon exposure to a specific gas (such as e.g. $SO_2$, HCl, $NO_2$). The change in optical properties may be enhanced by coupling between the nanoparticles and the gas-sensitive molecules. The change in optical properties of these molecules is characterized by the (dis)appearance of peaks in the absorption spectrum. Near the spectral position of these peaks, the refractive index changes rapidly as a function of wavelength. The changes in optical properties resulting from exposure to a gas may be detected by measuring the far field extinction spectrum of the nanoparticle array.

In preferred embodiments of the present disclosure the third dielectric layer 33 and the second dielectric layer 32 are porous layers with embedded gas sensitive molecules, and a nanoantenna array 30 is sandwiched between these porous dielectric layers 33, 32.

In embodiments of the present disclosure, the porosity of the sensing layer facilitates the diffusion of a gas to be detected (e.g. $NO_2$) into the sensing layer such that it can react with the gas sensitive molecules. The gas sensitive molecules are enabled to react with the gas, e.g. $NO_2$ gas, not only at the surface of the sensing layer, but in the entire volume of the layer. This approach therefore allows using a thicker sensing layer as compared to prior art devices, and thus allows and enables the detection of surface lattice resonances which may extend up to several hundreds of nanometers from the plane of the nanoparticles, realizing a gas sensor with an even higher sensitivity.

Figure 3:
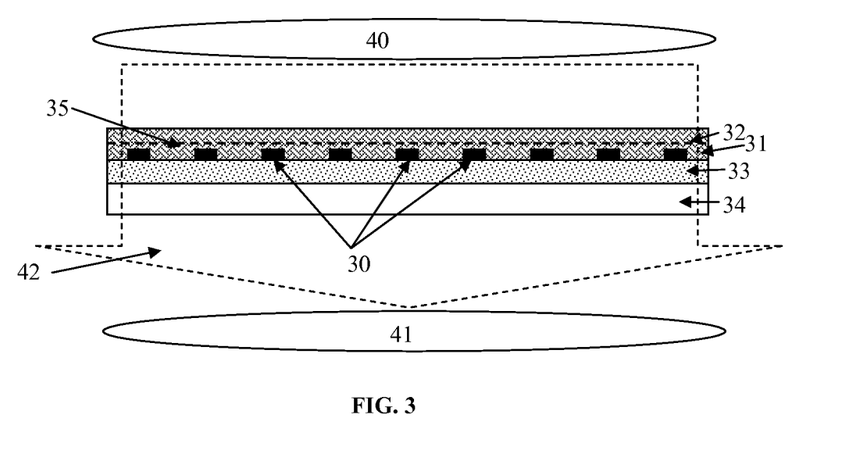
FIG. 3 schematically shows a gas sensing system for detecting a gas with the gas sensor according to FIG. 2.

FIG. 3 schematically illustrates a measurement set-up that can be used for detecting, e.g. a gas, by means of an optical sensor of the present disclosure. Light 42 from a light source 40, such as e.g. a laser or a LED (Light Emitting Device) is sent through an optical sensor of the present disclosure, e.g. in a direction perpendicular to a surface of the optical sensor. The transmitted light is detected by means of an optical detector 41, e.g. a photodiode. The measured transmission is equal to the intensity of the light source 40 minus the losses due to absorption (by the plasmons), reflection, and scattering. Dips in the transmission spectrum are present where surface lattice resonances occur. The gas sensitive molecules embedded in the porous dielectric layer 32 show a change in their optical properties upon exposure to a gas to be detected. Therefore, upon interaction with a gas to be detected, the resonance condition needed for long range coupling between the nanoparticles changes. The resonances shift due to a change in refractive index of the gas sensitive molecules upon gas absorption. The resonances may also be attenuated due to an increase in the extinction coefficient of the gas sensitive molecules upon gas absorption.

In embodiments of the present disclosure, the light source 40 preferably is a monochromatic light source or a light source with a narrow bandwidth. However, other light sources can be used, such as, for example, a white light source. An optical filter may be provided between the light source and the optical sensor.

Figure 4:
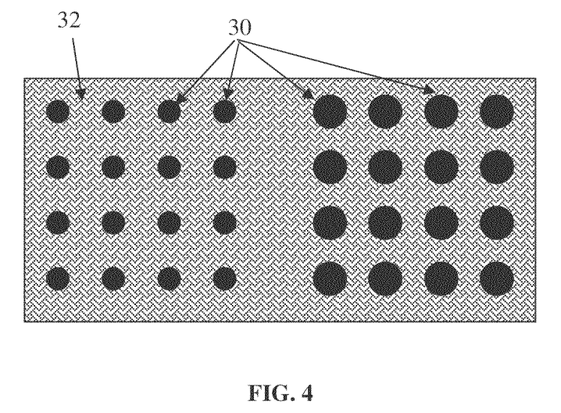
FIG. 4 schematically illustrates a gas sensor comprising two different nanoparticle arrays that exhibit surface lattice resonance in different conditions, according to an embodiment of the present disclosure.

In embodiments of the present disclosure, an optical sensor comprises different nanoparticle arrays that exhibit surface lattice resonance at different conditions. The surface lattice resonance depends on the particle size and the pitch of the nanoparticles in an array. Instead of measuring the entire transmission spectrum, the transmission intensity is measured at a single wavelength (e.g. using a laser as a light source 40) or within a narrow wavelength range (e.g. using a LED as a light source 40). If the resonance of the nanoparticles coincides with this wavelength, a transmission dip is measured, since power is lost into the surface lattice resonances. Not all nanoparticle arrays show a dip in transmission at that wavelength, but only the ones that are resonant. When the optical properties of the environment change, e.g. when the optical properties of the sensing layer 32 change due to gas absorption, the resonance condition changes. Nanoparticle arrays that were resonant before gas absorption at the wavelength of the light source 40 may not be resonant after gas absorption, while other nanoparticle arrays may become resonant under the new conditions. This effect is schematically illustrated in FIG. 4, showing a top view of an optical sensor comprising two nanoparticle arrays wherein, for example, before gas absorption one nanoparticle array can be resonant and after gas absorption the other nanoparticle array can be resonant. By monitoring which nanoparticle arrays are resonant, the presence of a gas in the sensing layer 32 can be detected. The concentration of the gas may be measured by monitoring the speed at which the nanoparticle resonance shifts.

In embodiments of the present disclosure wherein the optical sensor comprises at least two, e.g. a plurality of, nanoparticle arrays, a separate light source and/or detector may be provided for each nanoparticle array. Alternatively, a single light source may be used for illuminating more than one nanoparticle array and/or a single detector may be used for measuring the transmission of more than one nanoparticle array.

In embodiments of the present disclosure the shift in resonance is not detected by measuring the transmission spectrum directly, but by monitoring different nanoparticle arrays with different nanoparticle sizes and pitches. It is an advantage of this approach that it allows an easy read-out of the sensor and that the need for a spectrometer and/or a prism can be avoided.

The spectral position of the nanoparticle array resonance is preferably tuned such that it nearly coincides with the expected wavelength of the absorption peak of the gas-sensitive molecules after gas exposure. In other words, the nanoparticle sizes and pitches are selected such that their resonances cover the wavelength range of interest. Thus, upon gas exposure, the resonance condition of a nanoparticle array changes due to the increase or decrease of the refractive index of the embedded gas-sensitive molecules.

In embodiments of the present disclosure nanoantenna dimers, i.e. periodic arrays of closely separated nanoparticle pairs (or multiples), can be provided in the first layer. The separation between the nanoparticles within a pair is typically less than 100 nm. Such nanoparticle pairs have the advantage that between them, the optical near field intensity is strongly enhanced, which may enhance the sensitivity of the gas sensor. Furthermore, by tuning the separation between the nanoparticles within the pairs, the resonance wavelength can be tuned.

Figure 5:
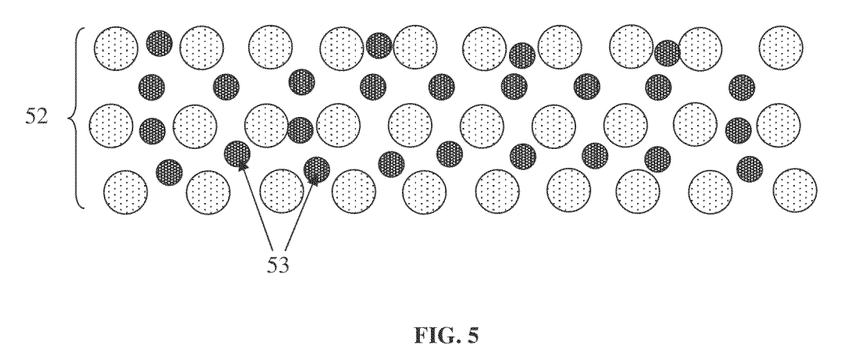
FIG. 5 schematically shows a cross section of a porous layer with embedded gas sensitive molecules.
Figure 6:
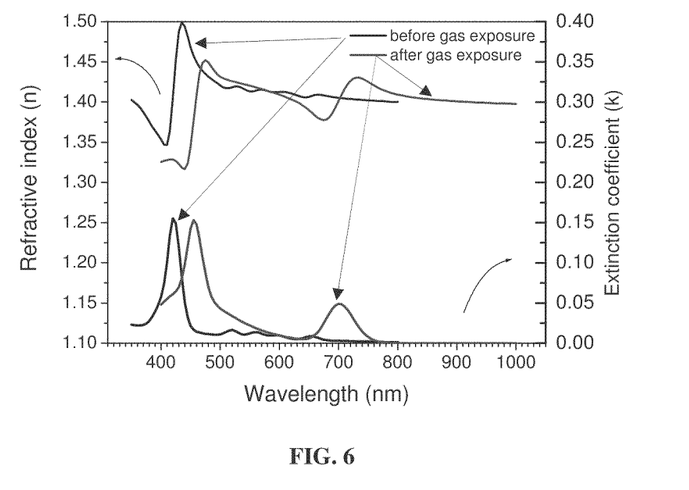
FIG. 6 shows the measured real and imaginary parts of a 130 nm thick layer of porous NCS with embedded 2H—OHTPP molecules.

Calculations were performed to investigate the effect of using porous dielectric layers (NCS) with embedded gas sensitive molecules in SPR based optical gas sensors. These calculations were performed with nanoparticle arrays as in embodiments of the present disclosure and a porous dielectric layer 52 comprising embedded gas sensitive molecules 53, as illustrated in FIG. 5. Changes of the refractive index of this porous dielectric layer with embedded molecules were determined by ellipsometry measurements (FIG. 6). In these experiments porphyrin molecules, more in particular. 5,10,15,20-Tetrakis(4-hydroxyphenyl)-21H,23H-porphine (2H—OHTPP), were used as gas sensitive molecules. 2H—OHTPP molecules show a change of the absorption spectrum upon exposure to a specific gas (such as e.g. $SO_2$, HCl, $NO_2$). FIG. 6 shows the measured (by ellipsometry) real and imaginary parts (n and K respectively) of the refractive index of a 130 nm thick porous NCS layer with embedded 2H—OHTPP molecules.

Figure 7A:
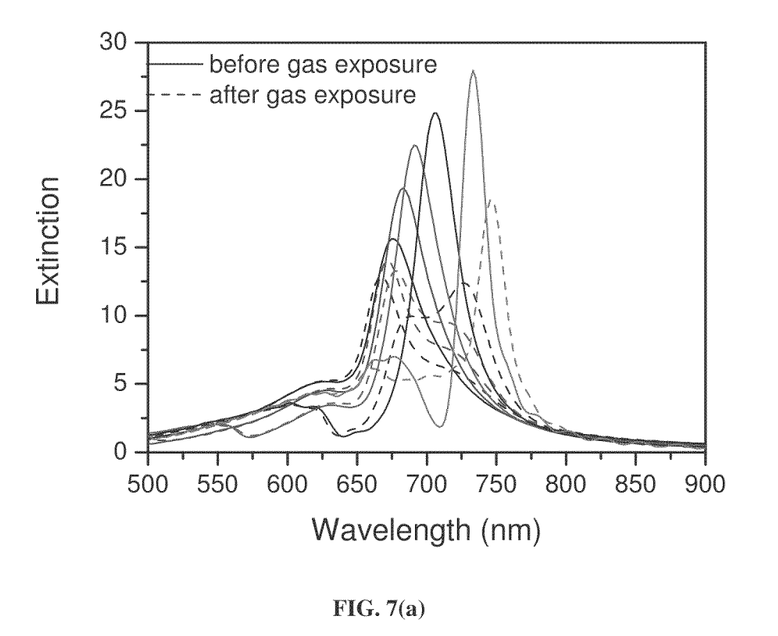
FIG. 7(a) shows results for nanoparticle arrays with periods from 300 nm to 500 nm, the nanoparticles having a diameter of 100 nm and a height of 40 nm.

To understand the changes of the surface lattice resonance during exposure to $NO_2$ gas, the evolution of the absorption spectrum of a layer of 2H—OHTPP in NCS was calculated using the optical constants as determined by ellipsometry. Modifications of the surface lattice resonance due to the change in absorption of the layer were then calculated for nanoparticle arrays with periods from 300 nm to 500 nm using a nanoparticle diameter of 100 nm and a height of 40 nm. The results are summarized in FIG. 7(a), showing the extinction as a function of wavelength before gas exposure (full lines) and after gas exposure (dashed lines). The resonance shifts to a higher wavelength for nanoparticle arrays having a larger period. From FIG. 7(a), it is clear that the absorption of the 2H—OHTPP in NCS layer around 700 nm results in spectral modifications of the surface lattice resonance. These modifications are characterized by a decrease in the transmission of the nanoparticle array at 700 nm, coinciding with the absorption peak wavelength of the prophyrins, and a shift of the resonances to shorter or longer wavelengths depending on their spectral position before gas exposure.

Figure 7B:
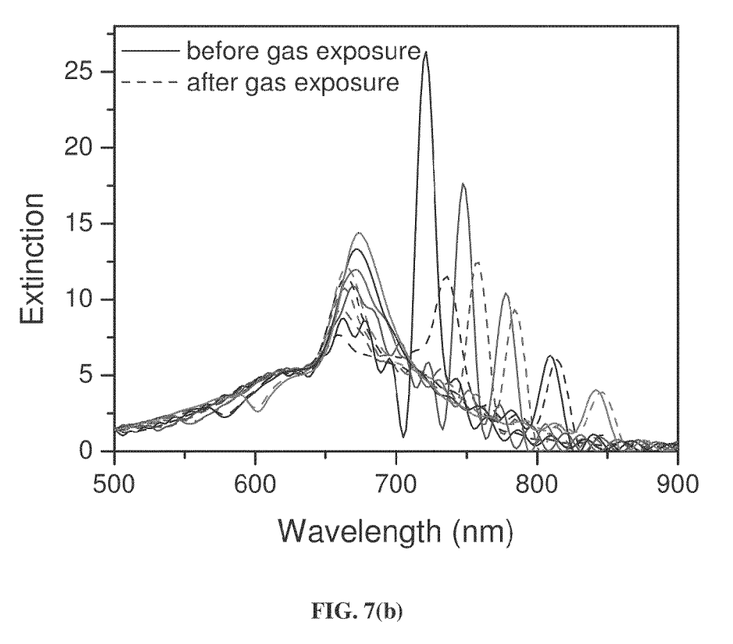
FIG. 7(b) shows results for nanoparticle arrays with periods from 600 nm to 700 nm, the nanoparticles having a diameter of 90 nm and a height of 40 nm.

FIG. 7(b) shows the extinction as a function of wavelength before gas exposure (full lines) and after gas exposure (dashed lines) for nanoparticle arrays with periods from 600 nm to 700 nm, the nanoparticles having a diameter of 90 nm and a height of 40 nm. A clear decrease in transmission can be seen after gas exposure for nanoparticle arrays that have resonances near 700 nm. Furthermore, a shift to longer wavelengths can be seen after gas exposure. The shift is largest (15 nm) for nanoparticle arrays that have resonances close to the absorption peak wavelength of the porphyrins.

Figure 8:
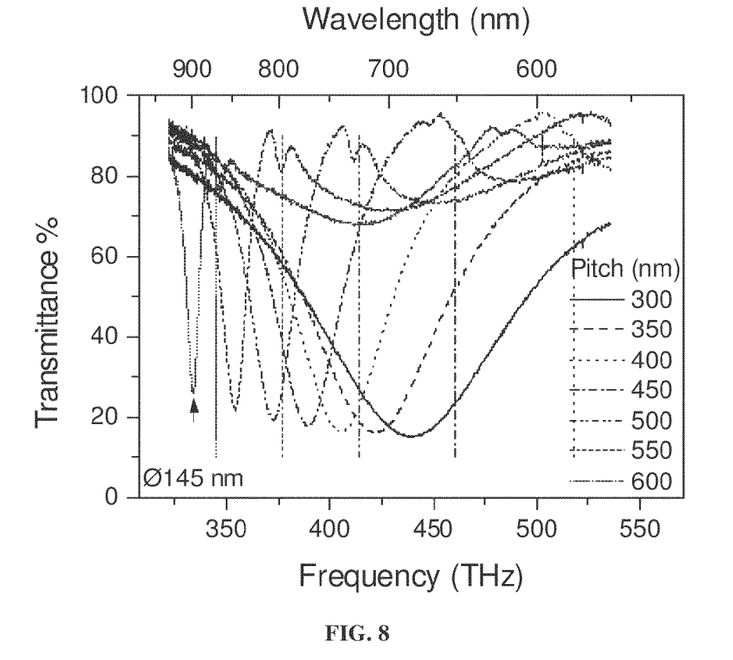
FIG. 8 shows transmittance spectra of gold nanoparticle arrays on quartz embedded in a liquid environment with n=1.45 as a function of frequency for different particle spacings (300 nm, 350 nm, 400 nm, 450 nm, 500 nm, 550 nm and 600 nm). The average particle size is 145 nm×145 nm×50 nm.

FIG. 8 shows transmittance spectra of gold nanoparticle arrays on quartz (refractive index n=1.45) embedded in a liquid environment with n=1.45 as a function of frequency for different particle spacings L (300 nm, 350 nm, 400 nm, 450 nm, 500 nm, 550 nm and 600 nm). The average particle size is 145 nm×145 nm×50 nm. The transmittance spectra was obtained by illuminating the sample with a collimated beam of white light from a halogen lamp at normal incidence. No specific polarization was used. The transmission was first measured through the arrays and normalized to the transmission through the quartz substrate. The spectra show strong dips reaching values of less than 20% in transmittance, that red-shift and narrow considerably with increasing array spacing. The vertical lines in FIG. 8 indicate the frequencies of the diffraction edges $v_{RA}=c/nL$, which represent the Rayleigh anomaly conditions at which diffracted orders become evanescent. The dips occur on the low-frequency side of the corresponding diffraction edge, while the transmittance reaches a maximum at frequencies close to $v_{RA}$. These are characteristic features of surface lattice modes which are formed by the coupling of surface plasmon resonances localized at each nanoparticle site to the Rayleigh anomaly. This gives rise to surface lattice resonances which correspond to the poles of the effective polarizability of the particles in the array. These modes can be modeled using the coupled-dipole approximation for an infinite array, in which the effective polarizability of each particle in the arrays is expressed as:

$$\alpha^* = \frac{1}{\frac{1}{\alpha} - S'}$$

where $\alpha$ is the polarizability of the individual particles and S' is the retarded dipole sum, which accounts for the contribution to $\alpha^*$ from all other dipoles in the array. With increasing lattice spacing, both the real and the imaginary part of S become more negative, leading to a red-shift of $v_{SPR}$ and a narrowing of the lattice resonances by partial cancellation of the radiative damping, thus explaining the trend observed in FIG. 8.

Figure 9:
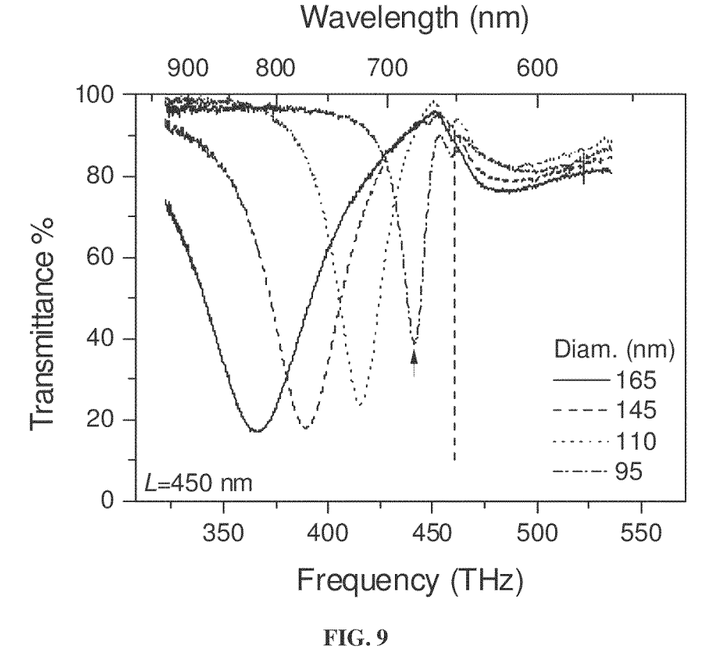
FIG. 9 shows transmittance spectra of gold nanoparticle arrays on quartz embedded in a liquid environment with n=1.45 as a function of frequency for different average particle diameters (95 nm, 110 nm, 145 nm and 165 nm). The particle spacing and height are 450 nm and 50 nm, respectively.

FIG. 9 shows transmittance spectra of gold nanoparticle arrays on quartz embedded in a liquid environment with n=1.45 as a function of the frequency for different average particle diameters d=95 nm, 110 nm, 145 nm and 165 nm. The particle spacing L and height were 450 nm and 50 nm, respectively. The vertical line corresponds to the diffraction edge with $v_{RA}=c/(1.45 L)$. The transmittance spectra was obtained by illuminating the sample with a collimated beam of white light from a halogen lamp at normal incidence. No specific polarization was used. The transmission was first measured through the arrays and normalized to the transmission through the quartz substrate. The resonances blue-shift with decreasing particle diameter and narrow as their resonance frequency approaches that of the Rayleigh anomaly, indicated by the vertical dashed line. For the surface lattice resonances indicated by the arrows in FIG. 8 and FIG. 9, the frequency difference between the Rayleigh anomaly and the surface lattice resonance, $v_{RA}-v_{SPR}$, and the resonance width are very similar. The frequency difference $v_{RA}-v_{SPR}$ can be seen as a scaling parameter that solely defines the FoM of a sensor based on surface lattice resonances. The parameter provides an indication of the coupling strength of the localized surface plasmon resonance to the Rayleigh anomaly. A consequence of the scaling is that, by tuning both the particle spacing and the particle diameter such that $v_{RA}-v_{SPR}$ remains constant, it is possible to shift resonances over a wide spectral range without affecting their width. This behavior is a major advantage for sensing applications as it enables the use of narrow resonances at specific predefined frequencies.

Figure 10:
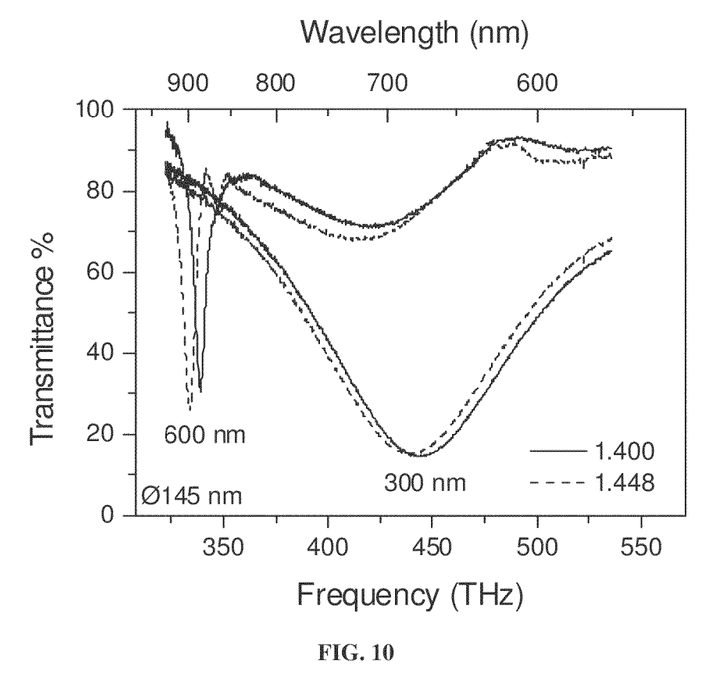
FIG. 10 shows transmittance spectra of two gold nanoparticle arrays with different particle spacing (300 nm and 600 nm) on quartz embedded in a liquid environment with n=1.40 (dashed lines) and n=1.45 (solid lines) as a function of frequency, illustrating increased sensitivity and a clear narrowing for the array with a particle spacing of 600 nm. Particle diameter and height are 145 nm and 50 nm, respectively.

FIG. 10 shows transmittance spectra for two gold nanoparticle arrays with different particle spacing L=300 nm and L=600 nm on quartz embedded in a liquid environment with n=1.40 (dashed lines) and n=1.45 (solid lines) as a function of the frequency, showing increased sensitivity and a clear narrowing for the array with L=600. Particle diameter and height are 145 nm and 50 nm, respectively. The transmittance spectra was obtained by illuminating the sample with a collimated beam of white light from a halogen lamp at normal incidence. No specific polarization was used. The transmission was first measured through the arrays and normalized to the transmission through the quartz substrate. Upon changing the refractive index of the environment, the resonances red-shift due to modification of the coupling condition between the incident plane wave and the surface lattice resonance. This shift results in an increased transmittance at the initial resonance frequency. The array with a lattice constant of 300 nm is characterized by a broad lattice resonance with a bulk sensitivity comparable to that of localized plasmon resonances found in disordered arrays of nanoparticles. The transmittance in this sample increases only a few percent when the refractive index is varied. In contrast, the array with a lattice constant of 600 nm shows a lattice resonance that is narrower by an order of magnitude with a bulk sensitivity that is almost two times higher, resulting in an increase in transmittance by more than 40%.

Figure 11:
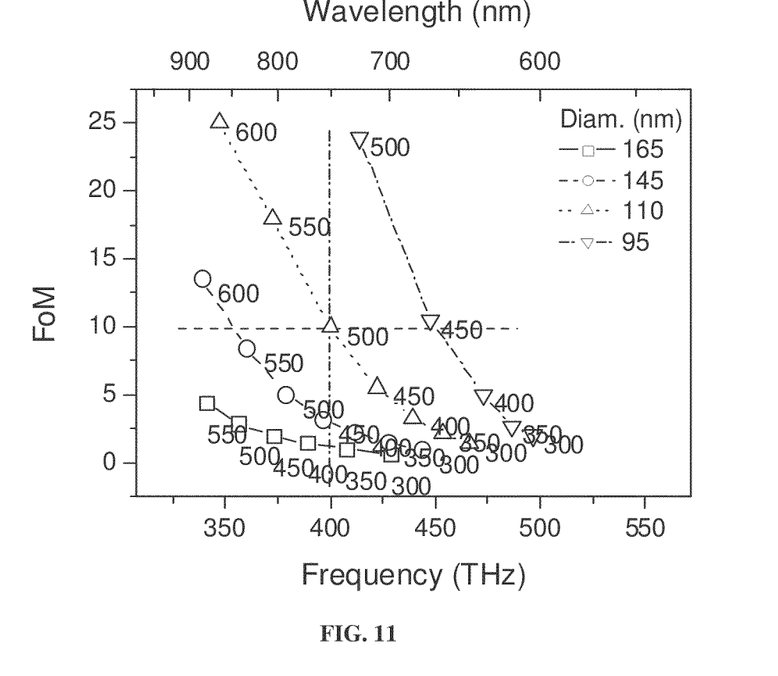
FIG. 11 shows a figure of merit (FoM) for particle arrays with diameters of 95 nm, 110 nm, 145 nm, and 165 nm, with a height of 50 nm and particle spacings of 300 nm, 350 nm, 400 nm, 450 nm, 500 nm, 550 nm and 600 nm indicated in the graph, as function of frequency.

FIG. 11 shows a FoM for particle arrays with diameters 95 nm, 110 nm, 145 nm and 165 nm, with height 50 nm and particle spacing L=300 nm, 350 nm, 400 nm, 450 nm, 500 nm, 550 nm and 600 nm indicated in the graph, as a function of frequency. The FoM characterizes the sensing performance of plasmonic structures and is expressed as FoM=$S_{bulk}/\Delta\lambda$, where $\Delta\lambda$ is the resonance width and $S_{bulk}$ is the bulk sensitivity defined as $S_{bulk}=\delta\lambda/\delta n$. The sensitivity describes the resonance wavelength shift as the refractive index n of the medium around the nanostructures changes. As expressed by the FoM, where the full-width at half-maximum of the resonance $\Delta\lambda$ appears in the denominator, narrow resonances are advantageous for sensing applications as they enable a much more accurate determination of the wavelength shift upon changes in the environment compared to broad resonances, by simply monitoring the variation in transmittance at a fixed wavelength close to resonance wavelength. The experimental FoM is plotted as a function of resonance frequency for nanoparticle arrays with different diameters and lattice constants. The FoM changes strongly as function of lattice constant and diameter from a value of about 1 to 2 for arrays with small lattice constant and large diameter, to values as high as 25 for arrays with large lattice constant and small diameter. This increase of the FoM by more than one order of magnitude illustrates the relevance of coupled plasmonic resonance for optical sensing. The resonance frequency can be tuned over a large range with the same FoM, by varying particle diameter and array spacing (indicated by the dashed line in FIG. 11). On the other hand, the FoM can be increased at a fixed resonance frequency, by tuning both particle diameter and array spacing (indicated by the dash-dotted line in FIG. 11).

Figure 12:
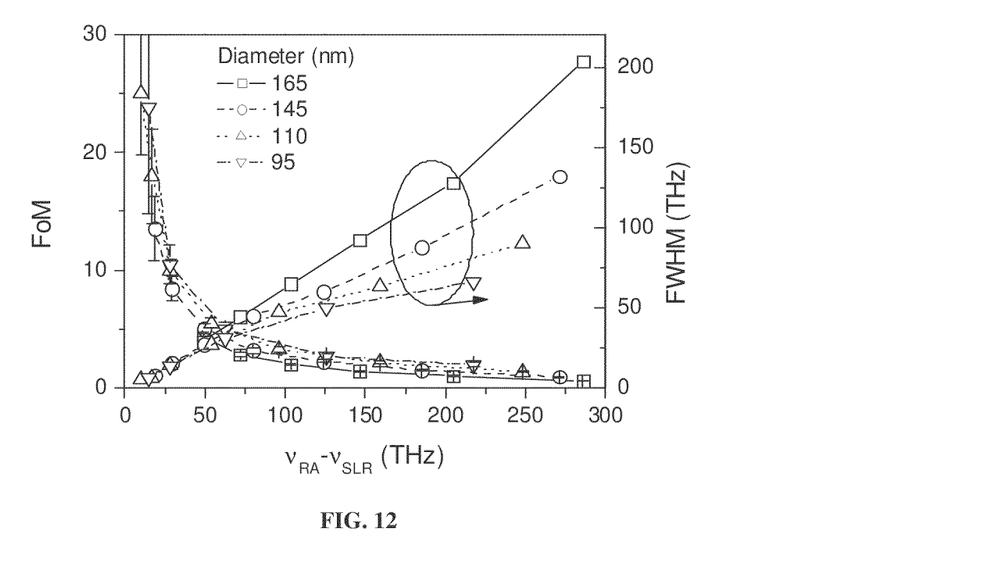
FIG. 12 shows the measured FoM and FWHM of particle arrays with diameters 95 nm, 110 nm, 145 nm, and 165 nm, height 50 nm and particle spacing 300 nm, 350 nm, 400 nm, 450 nm, 500 nm, 550 nm and 600 nm as function of the frequency difference of the Rayleigh anomaly and the surface lattice resonance ($v_{RA}-v_{SPR}$).

FIG. 12 shows the measured FoM and FWHM for particle arrays with diameters 95 nm, 110 nm, 145 nm, 165 nm, height 50 nm and particle spacing L=300 nm, 350 nm, 400 nm, 450 nm, 500 nm, 550 nm and 600 nm as function of $v_{RA}-v_{SPR}$. As indicated in FIG. 8 and FIG. 9, the width of the resonances is related to the difference between the resonance frequency and that of the Rayleigh anomaly $v_{RA}-v_{SPR}$. To investigate this dependency, the FoM and the FWHM are plotted as function of $v_{RA}-v_{SPR}$ in FIG. 12. The FoM is only determined by $v_{RA}-v_{SPR}$, despite large variations in lattice constant and particle diameter. The increase in the FoM at smaller $v_{RA}-v_{SPR}$ is paired with a decreasing FWHM, while at larger $v_{RA}-v_{SPR}$ an increasing spread in the FWHM can be observed. The spread in the FWHM is attributed to an increasing influence of radiative damping and depolarization with particle diameter. The absence of spread in the FoM at larger $v_{RA}-v_{SPR}$ may be attributed to a compensating behavior of the bulk sensitivity as function of $v_{RA}-v_{SPR}$. Thus, the FoM is ultimately governed by the detuning of the surface lattice resonance with the Rayleigh anomaly. It may be increased by decreasing the particle size and increasing the array spacing for any desired wavelength of the resonance. However, there may be an optimum in the FoM due to a decreased mode strength which is induced by the presence of the substrate for small nanoparticle diameters or large spacing, as this results in a decreased extinction at the resonance position.

Figure 13:
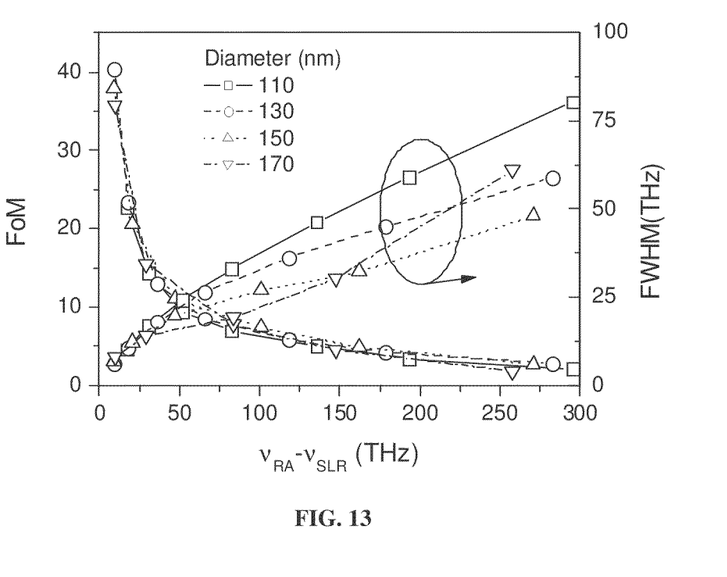
FIG. 13 shows the calculated FoM and FWHM of particle arrays with diameters 110 nm, 130 nm, 150 nm, and 170 nm, height 50 nm and particle spacing 300 nm, 350 nm, 400 nm, 450 nm, 500 nm, 550 nm and 600 nm as function of $v_{RA}-v_{SPR}$.

FIG. 13 shows the calculated FoM and FWHM for particle arrays with diameters 110 nm, 130 nm, 150 nm and 170 nm, height 50 nm and particle spacing L=300 nm, 350 nm, 400 nm, 450 nm, 500 nm, 550 nm and 600 nm as function of $v_{RA}-v_{SPR}$. The FoM scales inversely proportional with $v_{RA}-v_{SPR}$ despite a large variation in both array spacing and particle diameter. The calculation was performed using an FDTD method for nanoparticles embedded in a homogeneous environment. The results are in qualitative agreement with the experimental data of FIG. 12, supporting the observed trends.

It has been demonstrated above that by optimizing both the particle spacing and their diameter it is possible to shift the resonances over a wide spectral range without affecting their width. This enables the use of these structures in plasmonic/optical sensors that need tuning towards specific wavelengths. These structures can be used for gas sensing based on gas-induced molecular resonances. In this scheme, the surface lattice resonance is tuned to the wavelength of a gas-induced absorption peak of a gas-sensitive molecule. Then, in the presence of gas, the induced molecular resonance couples to the surface lattice resonance, leading to an observable shift in the surface plasmon resonance.

Experiments were performed wherein nanoparticles were embedded in a nanoporous layer of a siliconoxicarbide (NPS), containing 5,10,15,20-Tetrakis(4-hydroxyphenyl)-21H,23H-porphine (OH-TPP) as the gas-sensitive molecule. OH-TPP was dissolved in ethanol in a concentration of 5 g/l. NPS was mixed with the OH-TPP solution (1:1) and further diluted (1:1) with ethanol. This solution was spin-coated on substrates with gold nanoparticle arrays and baked out at 200° C. for 30 seconds. The procedure was repeated until a thickness of 440 nm was achieved.

Figure 14:
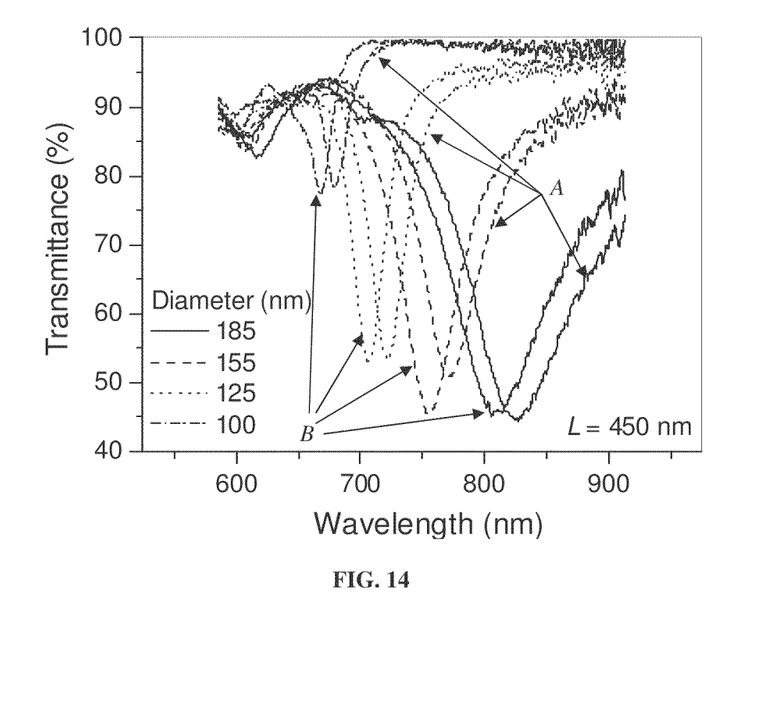
FIG. 14 shows transmittance spectra of nanoparticle arrays with varying diameter and a constant pitch of 450 nm before and after exposure to a saturating concentration of $NO_2$ in $N_2$. The nanoparticles are covered with a sensing layer consisting of a 440 nm thick nanoporous siliconoxicarbide layer with embedded 5,10,15,20-Tetrakis(4-hydroxyphenyl)-21H,23H-porphine molecules.

The change in transmittance of the gold nanoparticle arrays covered by the sensing layer was measured before and after exposure to a saturating concentration of $NO_2$ in $N_2$. The transmittance spectra of nanoparticle arrays with varying diameter and constant pitch of 450 nm are shown in FIG. 14, before gas exposure (B) and after gas exposure (A). Gas exposure results in a red-shift of the transmittance spectra which may be explained by the increase in refractive index of the sensing layer upon gas exposure, as indicated by ellipsometry data. The accompanying increase in transmittance, measured at the wavelength of the surface lattice resonance before gas exposure, is up to 20% for the nanoparticle arrays with a diameter of 100 nm and 125 nm, demonstrating the feasibility of $NO_2$ sensing with gold nanoparticle arrays.

What is claimed is:

1. A gas sensor, comprising:
a first layer and a second layer superimposed on each other and having an interface between the two layers, the first layer comprising an array of nanoparticles formed along the interface, the nanoparticles being provided so as to allow, upon illumination with electromagnetic radiation, a long range diffractive coupling of surface plasmon resonances resulting in a surface lattice resonance condition, the surface lattice resonance condition having an evanescent field associated therewith, the evanescent field having a decay length, the second layer comprising a material that, responsive to exposure to at least one predetermined gas, detectably affects the surface lattice resonance condition,
wherein the second layer material has a porosity of at least 10%, and wherein the second layer is at least as thick as the decay length of the evanescent field associated with the surface lattice resonance condition.

2. The gas sensor as claimed in claim 1, wherein the second layer and the nanoparticles are respectively made of materials having dielectric constants of opposing sign.

3. The gas sensor as claimed in claim 2, wherein the nanoparticles are made of metal.

4. The gas sensor as claimed in claim 3, wherein the metal is gold.

5. The gas sensor as claimed in claim 1, wherein the nanoparticles are made of a material having a complex permittivity with an imaginary part equal to or larger than the real part.

6. The gas sensor as claimed in claim 1, wherein the material of the second layer is a dielectric.

7. The gas sensor as claimed in claim 1, wherein the gas sensor further comprises a second nanoparticle array, the first nanoparticle array having a first surface lattice resonance condition and the second nanoparticle array having a second surface lattice resonance condition different from the first.

8. The gas sensor as claimed in claim 1, wherein the gas sensor comprises a plurality of said nanoparticle arrays, each having a different surface lattice resonance condition.

9. The gas sensor as claimed in claim 1, wherein the first layer is sandwiched between the second layer and a third transparent dielectric layer.

10. The gas sensor as claimed in claim 9, wherein the third layer and the second layer are substantially optically symmetric.

11. The gas sensor as claimed in claim 1, wherein the material of the second layer substantially completely fills up spaces between the nanoparticles in the first layer.

12. The gas sensor as claimed in claim 1, wherein the second layer comprises gas sensitive molecules.

13. The gas sensor as claimed in claim 12, wherein the gas sensitive molecules include redox-active molecules.

14. The gas sensor as claimed in claim 13, wherein the redox-active molecules include porphyrin molecules.

15. The gas sensor as claimed in claim 14, wherein the porphyrin molecule is 5,10,15,20-Tetrakis(4-hydroxyphenyl)-21H,23H-porphine.

16. The gas sensor as claimed in claim 1, wherein the second layer comprises open pores.

17. The gas sensor as claimed in claim 1, wherein the second layer is a nano-clustered silica layer (NCS).

18. A method for optically measuring the presence of a gas, the method comprising:
illuminating a first layer of an optically transparent gas sensor with electromagnetic radiation from a radiation source, wherein the first layer comprises an array of nanoparticles that allow, upon illumination with electromagnetic radiation, a long range diffractive coupling of surface plasmon resonances resulting in a surface lattice resonance condition, the surface lattice resonance condition having an evanescent field associated therewith, the evanescent field having a decay length; and detecting, via a detector positioned such that the gas sensor is between the radiation source and the detector, changes in the electromagnetic radiation transmitted through the gas sensor caused by a change in the surface lattice resonance condition when a second layer is exposed to a gas, wherein the second layer comprises a material that detectably affects the surface lattice resonance condition when exposed to the gas, wherein the second layer material has a porosity of at least 10%, and wherein the second layer is at least as thick as the decay length of the evanescent field associated with the surface lattice resonance condition.

19. The method for optically measuring the presence of a gas according to claim 18, wherein the detector detects changes in the transmitted electromagnetic radiation at a single wavelength and a small wavelength band.

20. A gas sensing system comprising:

an optically transparent gas sensor, the gas sensor comprising a first layer and a second layer superimposed on each other and having an interface between the two layers, the first layer comprising an array of nanoparticles formed along the interface, the nanoparticles being provided so as to allow, upon illumination with electromagnetic radiation, a long range diffractive coupling of surface plasmon resonances resulting in a surface lattice resonance condition, the surface lattice resonance condition having an evanescent field associated therewith, the evanescent field having a decay length, the second layer comprising a material that, responsive to exposure to at least one predetermined gas, detectably affects the surface lattice resonance condition, wherein the second layer material has a porosity of at least at least 10%, and wherein the second layer is at least as thick as the decay length of the evanescent field associated with the surface lattice resonance condition;

a source of electromagnetic radiation for illuminating the gas sensor; and a detector positioned such that the gas sensor is between the radiation source and the detector, the detector being configured to detect changes in the electromagnetic radiation transmitted through the gas sensor caused by a change in the surface lattice resonance condition when the second layer is exposed to the predetermined gas.

* * * * *